(12) United States Patent
Shinno

(10) Patent No.: US 8,506,163 B2
(45) Date of Patent: Aug. 13, 2013

(54) X-RAY CT APPARATUS AND CONTROL METHOD OF X-RAY CT APPARATUS

(75) Inventor: Toshiyuki Shinno, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 207 days.

(21) Appl. No.: 12/966,381

(22) Filed: Dec. 13, 2010

(65) Prior Publication Data
US 2011/0142196 A1 Jun. 16, 2011

(30) Foreign Application Priority Data

Dec. 14, 2009 (JP) ................................ 2009-283051
Nov. 25, 2010 (JP) ................................ 2010-261972

(51) Int. Cl.
*A61B 6/08* (2006.01)
(52) U.S. Cl.
USPC ........................................ 378/206; 378/207
(58) Field of Classification Search
USPC ...................................... 378/4–20, 205–207
See application file for complete search history.

(56) References Cited

U.S. PATENT DOCUMENTS 5,188,110 A * 2/1993 Sugimoto ..................... 600/425
7,170,967 B2 * 1/2007 Cherek et al. ................... 378/20

FOREIGN PATENT DOCUMENTS

JP 2006-122479 5/2006

* cited by examiner

*Primary Examiner* — Hoon Song
(74) *Attorney, Agent, or Firm* — Oblon, Spivak, McClelland, Maier & Neustadt, L.L.P.

(57) ABSTRACT

An X-ray CT apparatus has a plurality of projectors, a reception unit, a setting unit, a supporter, and a scan execution unit. The projectors each have a light source on a circumference having a same radius as a rotation radius of an X-ray focal point of an X-ray irradiator and each irradiate laser light having an irradiation range simulating an irradiation range of the X-ray. The reception unit receives an instruction for three-dimensionally sliding the projectors as one body. The setting unit sets a position of the projectors. The supporter supports a table and three-dimensionally slides the table by a difference between a position of a center of the circumference of the set projectors and a position of a rotation center of the X-ray focal point of the X-ray irradiator. The scan execution unit executes a scan with the table after the sliding as a scan position.

13 Claims, 8 Drawing Sheets

X-RAY CT APPARATUS AND CONTROL METHOD OF X-RAY CT APPARATUS

CROSS-REFERENCE TO RELATED APPLICATION

This application is based upon and claims the benefit of priority from Japanese Patent Application No. 2009-283051, filed on Dec. 14, 2009, and Japanese Patent Application No. 2010-261972, filed on Nov. 25, 2010, the entire contents of which are incorporated herein by reference.

FIELD

The present embodiment as one state of the present invention relates to an X-ray CT (computed tomography) apparatus and a control method of the X-ray CT apparatus that irradiate an X-ray and detect the X-ray transmitted through an object for imaging.

BACKGROUND

In conventional X-ray CT apparatuses, it is necessary to previously make a scan plan before actually starting data acquisition by a main scan, such as a dynamic scan. In the scan plan, X-ray tube voltage, X-ray tube current, slice thickness, a cone angle, a fan angle, a gantry tilt angle, a reconstruction matrix, a main scan position, and a main scan range from a scan start position to a scan end position to be used in the main scan are set. In order to set main scan conditions, such as the main scan position and the main scan range, in the scan plan, a scanogram scan (prescan) is performed, while a table-top on which a patient is placed is moved in a body axis direction of the patient, with rotation of an X-ray tube and a detector stopped. When scanograms are obtained by the scanogram scan, the main scan conditions, such as the main scan position and the main scan range, are designated using these scanograms. Therefore, it is necessary to irradiate an X-ray to the patient at a stage of the scan plan, and there is a disadvantage that an amount of exposure of the patient to radiation increases.

Therefore, an X-ray CT apparatus that can be easily operated, while suppressing unnecessary exposure of the patient to radiation at the stage of the scan plan, is proposed. This X-ray CT apparatus has a bed mechanism, an X-ray source, a detector, a gantry, a position setting unit, a positional relationship detecting unit, and a scanogram scan control unit. The bed mechanism has a table-top on which the patient is placed and which is movable in a body axis direction of the patient. The X-ray source is for irradiating an X-ray to the patient. The detector is for detecting the X-ray transmitted through the patient. The gantry is located so that the X-ray source and the detector rotate, being opposed to each other, with the patient sandwiched between them. The position setting unit sets any positions of the patient or the table-top for designating a plurality of regions of the patient. The positional relationship detecting unit detects positional relationships between the plurality of regions and the gantry, based on the set positions. The scanogram scan control unit continuously obtains scanograms for each of the plurality of regions by performing a scan, while moving the table-top, while switching irradiation and stop of an X-ray from the X-ray source, based on the detected positional relationships.

In addition, there is a case where alignment is performed by irradiating laser light to a portion corresponding to a center line of an X-ray irradiation range of the main scan, using a projector, in patient setting in an X-ray CT apparatus. In this case, the projector indicates only the center line of the X-ray irradiation range at a main scan position, and therefore, a health professional cannot accurately recognize the X-ray irradiation range, for example, when the main scan is performed using a multi-slice detector.

BRIEF DESCRIPTION OF THE DRAWINGS

In accompanying drawings.

DETAILED DESCRIPTION

An X-ray CT apparatus and a control method of the X-ray CT apparatus in present embodiment will be described with reference to the accompanying drawings.

To solve the above-described problems, the X-ray CT apparatus of the present embodiment has: an X-ray irradiator configured to irradiate an X-ray; an X-ray detector configured to detect the irradiated X-ray; a table on which an object is placed; a rotation control unit configured to rotate the X-ray irradiator and the X-ray detector as one body around the object; a plurality of projectors each having a light source on a circumference having a same radius as a rotation radius of an X-ray focal point of the X-ray irradiator and each configured to irradiate laser light having an irradiation range simulating an irradiation range of the X-ray; a reception unit configured to receive an instruction for three-dimensionally sliding the plurality of projectors as one body; a setting unit configured to set a position of the plurality of projectors by sliding the plurality of projectors based on the instruction; a supporter configured to support the table and three-dimensionally slide the table by a difference between a position of a center of the circumference of the set plurality of projectors and a position of a rotation center of the X-ray focal point of the X-ray irradiator; and a scan execution unit configured to execute a scan with the table after the sliding as a scan position.

To solve the above-described problems, the control method of the X-ray CT apparatus of the present embodiment has: a first step of receiving an instruction for three-dimensionally sliding a plurality of projectors as one body, which each has a light source on a circumference having a same radius as a rotation radius of an X-ray focal point of an X-ray irradiator which irradiates an X-ray and each irradiates laser light having an irradiation range simulating an irradiation range of the X-ray; a second step of setting a position of the plurality of projectors by sliding the plurality of projectors based on the instruction; a third step of three-dimensionally slide a table on which an object is placed, by a difference between a position of a center of the circumference of the set plurality of projectors and a position of a rotation center of the X-ray focal point of the X-ray irradiator; and a fourth step of executing a scan with the table after the sliding as a scan position.

Figure 1:
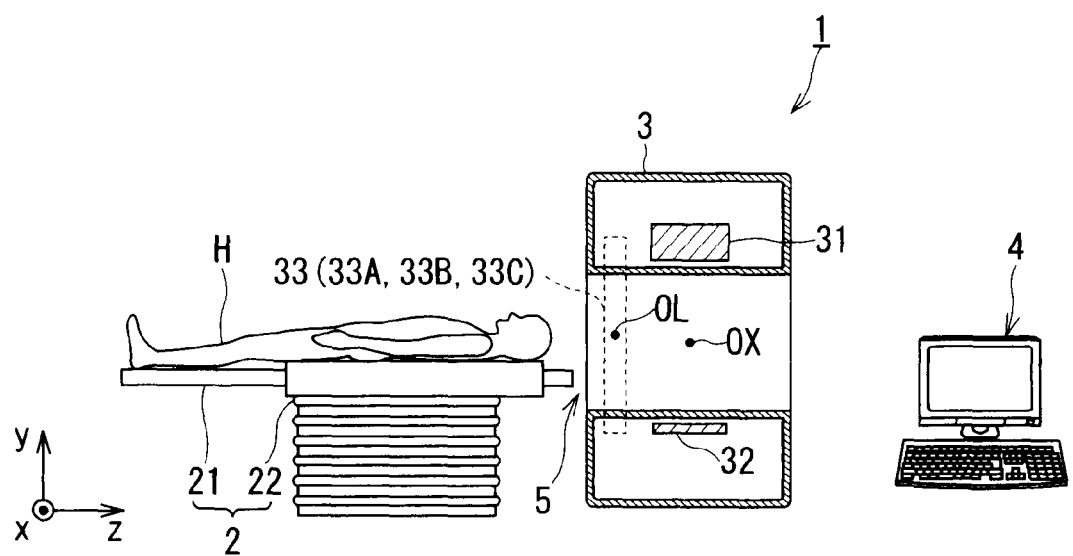
FIG. 1 is a configuration diagram showing an outline of an X-ray CT apparatus of a present embodiment.
Figure 2:
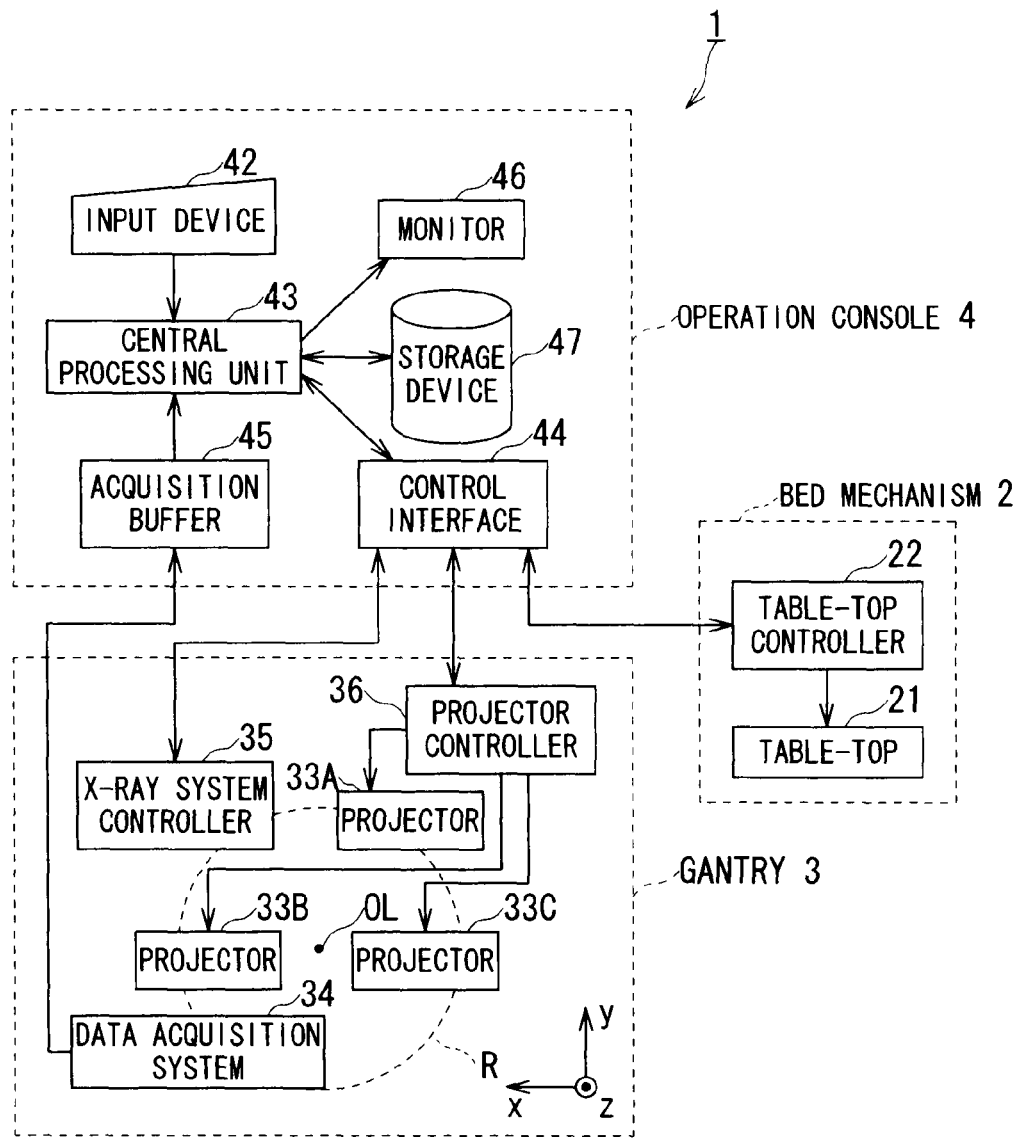
FIG. 2 is a block diagram showing a configuration of the X-ray CT apparatus according to the present embodiment.

FIG. 1 is a configuration diagram showing an outline of the X-ray CT apparatus of a present embodiment. FIG. 2 is a block diagram showing a configuration of an X-ray CT apparatus of the present embodiment.

As shown in FIG. 1 and FIG. 2, the X-ray CT apparatus 1 mainly has a bed mechanism 2 on which a patient (object H) is placed, a gantry 3 which irradiates an X-ray to the object H in photographing, and an operation console 4 which controls operations of the bed mechanism 2 and the gantry 3 and generates image data based on data acquired by the gantry 3.

The bed mechanism 2 has a table-top 21 and a table-top controller 22.

The object H can be placed on top of the table-top 21.

The table-top controller 22 slides the table-top 21 in a left and right direction (x-axis direction), body axis direction (z-axis direction), and up and down direction (y-axis direction) of the object H, with the object H placed on the table-top 21. The table-top controller 22 performs sending and receiving of control information between the operation console 4 and the bed mechanism 2 via a control interface 44 (described later) of the operation console 4. Thus, a health professional can remotely control the bed mechanism 2, using the operation console 4.

The gantry 3 has a cylindrical cavity portion (dome) passing through its interior and has an exit port 5 through which the table-top 21 on which the object H is placed can enter and exit this cavity portion. The opening of the exit port 5 should be, for example, widened in a tapered manner. The table-top 21 on which the object H is placed carries the object H in and out of the interior of the gantry 3 by sliding in the z-axis direction and entering and exiting the gantry 3 via the exit port 5.

The gantry 3 has an X-ray source 31, a detector 32, and a projector unit 33, as shown in FIG. 1. A rotation center OX of an X-ray focal point of the X-ray source 31 is formed in a central portion of the gantry 3.

The X-ray source 31 generates an X-ray by colliding against an electron beam with a target made of metal in response to a supplied tube voltage, and irradiates the X-ray toward the detector 32. The X-ray output from the X-ray source 31 traverses the cavity portion of the gantry 3 and is detected by the detector 32.

The detector 32 is a one-dimensional array detector (also referred to as a single-slice detector) having a plurality of detection elements in a channel direction and a single detection element in a row (slice) direction. Alternatively, the detector 32 is a two-dimensional array detector (also referred to as a multi-slice detector) which is a matrix type, that is, having X-ray detection elements in a plurality of channels in a channel direction and in a plurality of rows in a slice direction. The X-ray detection element of the detector 32 detects an X-ray irradiated from the X-ray source 31. A case where the detector 32 is a multi-slice detector will be described below. Data detected by the detector 32 is sent from a data acquisition system (DAS) 34 shown in FIG. 2 to a data acquisition buffer 45 (described later) of the operation console 4.

When the object H on the table-top 21 is placed in the gantry 3, the X-ray source 31 and the detector 32 rotate around a z-axis, and thus, a scan site of the object H is scanned. In addition, the gantry 3 is moved in the z-axis direction by a rail mechanism (not shown), and thus, the scan site of the object H placed inside the gantry 3 is intermittently scanned.

The projector unit 33 is built in the gantry 3. But, the projector unit 33 may be provided outside the gantry 3. The projector unit 33 has a plurality of projectors, for example, three projectors 33A to 33C. Each light source of the projectors 33A to 33C of the projector unit 33 is located on a circumference R (shown in FIG. 2) in an x-y plane (a plane perpendicular to the z-axis). A radius of the circumference R on which each light source of the projectors 33A to 33C is located is designed to be the same as a rotation radius of the X-ray focal point of the X-ray source 31. Here, a center of the circumference R on which each light source of the projectors 33A to 33C is located is defined as a projection center OL. It is desired that the projector unit 33 is provided closer to the bed mechanism 2 than the X-ray source 31 is.

Each of the projectors 33A to 33C of the projector unit can output laser light. An irradiation range of laser light simulates an irradiation range of an X-ray. The health professional can regard the irradiation range of laser light as the irradiation range of an X-ray. Location of the projector unit 33, and the irradiation range of laser light will be described later referring to FIG. 3.

The operation console 4 is configured based on a computer and has an input device 42, a central processing unit 43, a control interface 44, the acquisition buffer 45, a monitor 46, and a storage device 47.

The input device 42 inputs instructions, information, and the like from the health professional. The input device 42 may be provided on the periphery of the bed mechanism 2 and the gantry 3, or may be remotely provided.

The central processing unit 43 executes image reconstruction processing, a photographing sequence, and the like.

The control interface 44 outputs control signals and the like to the bed mechanism 2 and the gantry 3, based on the central processing unit 43.

The acquisition buffer 45 acquires data acquired by the data acquisition system 34 of the gantry 3.

The monitor 46 displays images and the like, based on control of the central processing unit 43.

The storage device 47 stores various data and programs.

In addition, as shown in FIG. 2, the gantry 3 has an X-ray system controller 35 which sends and receives control information for an X-ray scan to and from the operation console 4. The X-ray system controller 35 allows the health professional to remotely control the gantry 3, using the operation console 4. Further, the gantry 3 has a projector controller 36 which sends and receives control signals for the projectors 33A to 33C. The projector controller 36 allows the health professional to remotely control the projectors 33A to 33C, using the operation console 4.

Figure 3:
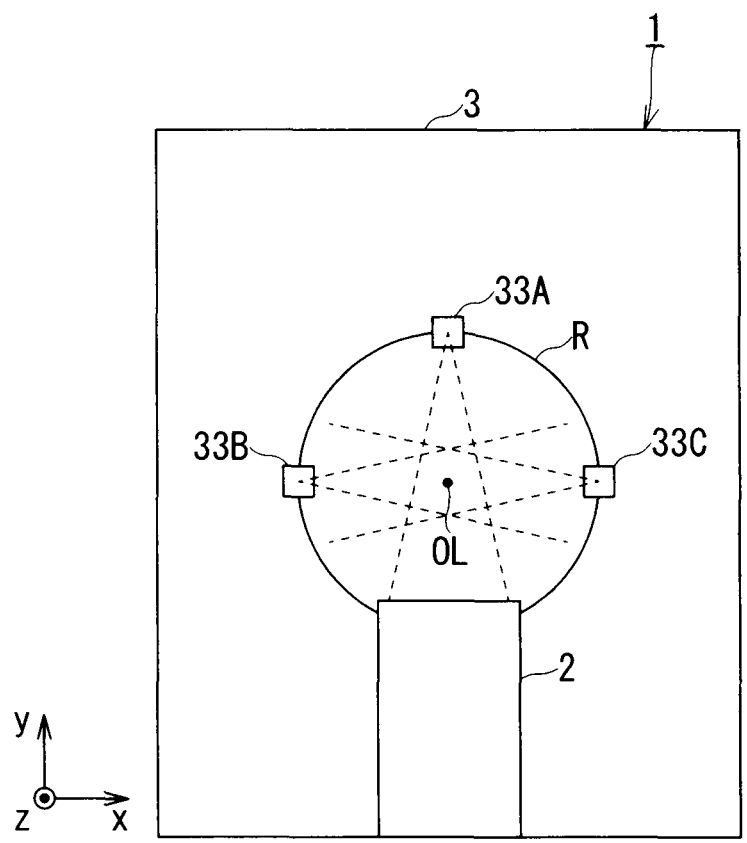
FIG. 3 is a diagram showing an example of location of a projector unit in the X-ray CT apparatus of the present embodiment.

FIG. 3 is a diagram showing an example of location of the projector unit 33 in the X-ray CT apparatus 1 of the present embodiment.

FIG. 3 is a diagram (x-y plane view) of the projector unit 33 as viewed from the bed mechanism 2 side. The projectors 33A to 33C of the projector unit 33 irradiate laser light simulating the irradiation range of an X-ray.

First, location of the projectors 33A to 33C for forming laser light simulating the irradiation range of the X-ray will be described. For example, the projector 33A is located at an upper end position on the circumference R corresponding to a view angle of the X-ray source 31 being 0 degree (upper end position), as shown in FIG. 3. In addition, for example, the projectors 33B and 33C are respectively located at left and right end positions on the circumference R corresponding to the view angle of the X-ray source 31 being 90 degrees and 270 degrees (left and right end positions, just beside the object H), as shown in FIG. 3.

Secondly, a direction of laser light for forming laser light simulating the irradiation range of the X-ray will be described. The projector 33A irradiates laser light from an upper portion of the gantry 3 so that the projection center OL is an irradiation center, as shown in FIG. 3, as in the case where the view angle of the X-ray source 31 is 0 degree. The projectors 33B and 33C irradiate laser light from side portions of the gantry 3 so that the projection center OL is the irradiation center, as shown in FIG. 3, as in the cases where the view angle of the X-ray source 31 is 90 degrees and 270 degrees.

Thirdly, a shape of laser light for forming laser light simulating the irradiation range of the X-ray will be described. Laser light from the projector 33A forms a quadrangular pyramid with the light source of the projector 33A as an apex, as in the case where the view angle of the X-ray source 31 is 0 degree. Two sides of a bottom surface of the quadrangular pyramid formed by the laser light from the projector 33A are parallel to an x-axis and the z-axis, respectively. Laser light from the projectors 33B and 33C forms quadrangular pyramids with the light sources of the projectors 33B and 33C as an apex, respectively, as in the cases where the view angle of the X-ray source 31 is 90 degrees and 270 degrees. Two sides of a bottom surface of the quadrangular pyramid formed by the laser light from the projector 33B (projector 33C) are parallel to the x-axis and a y-axis, respectively.

Figure 4:
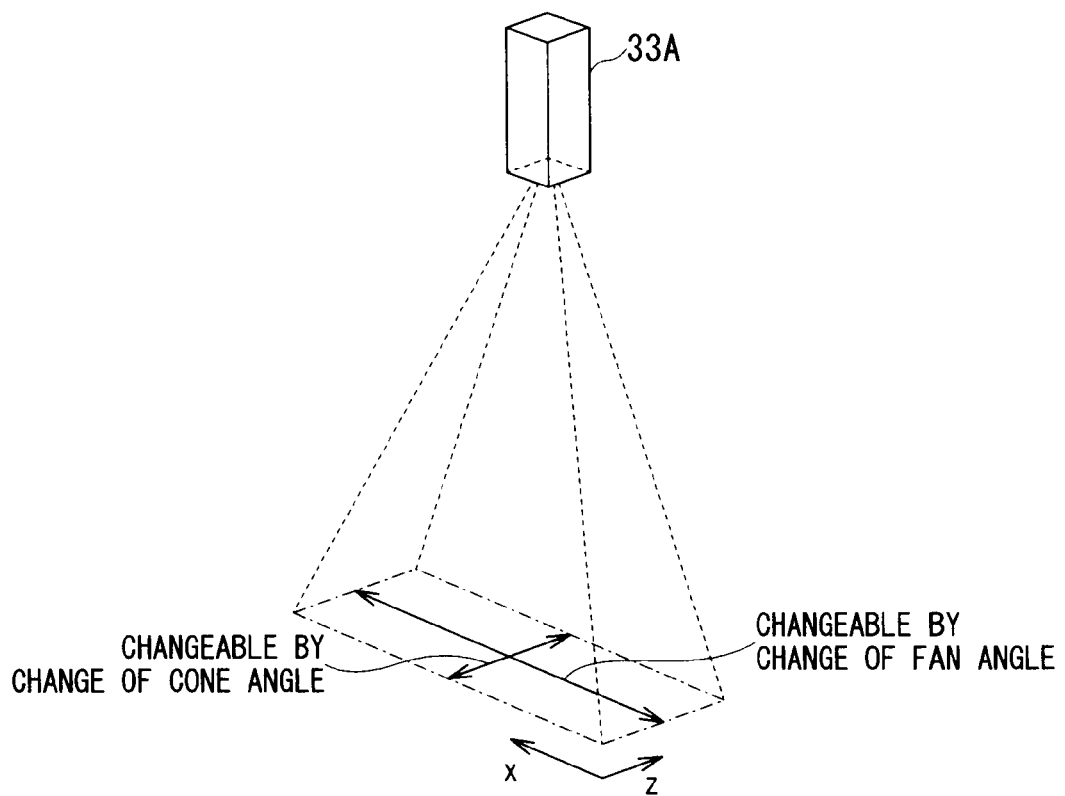
FIG. 4 is a diagram showing a shape of laser light irradiated from a light source of one projector of the projector unit in the X-ray CT apparatus of the present embodiment.

FIG. 4 is a diagram showing a shape of laser light irradiated from the light source of one projector 33A of the projector unit 33 in the X-ray CT apparatus 1 of the present embodiment.

As shown in FIG. 4, the laser light irradiated from the light source of the projector 33A of the projector unit 33 forms a quadrangular pyramid with the light source as an apex. In the projector 33A, when an irradiation angle (cone angle) is changed by control of the projector controller 36, a length of a bottom surface of the quadrangular pyramid in the z-axis direction is changed, and when an irradiation angle (fan angle) is changed, a length of the bottom surface of the quadrangular pyramid in the x-axis direction is changed. It is assumed that cone angles of the projectors 33A to 33C are always equal, and fan angles of the projectors 33A to 33C are always equal.

Figure 5:
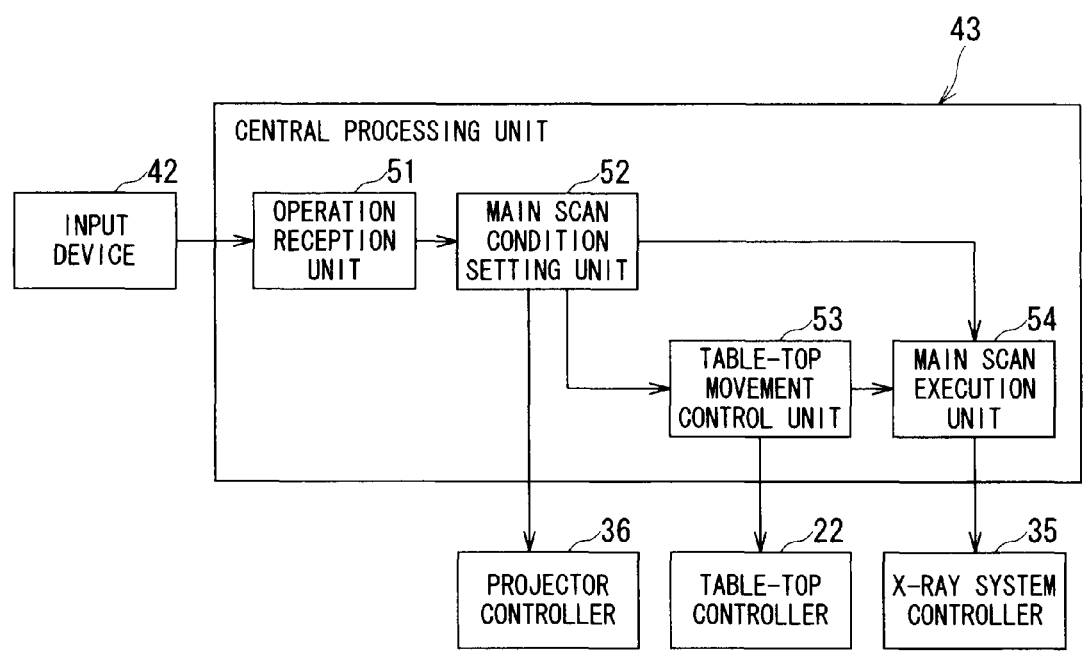
FIG. 5 is a block diagram showing functions of the X-ray CT apparatus of the present embodiment.

FIG. 5 is a block diagram showing functions of the X-ray CT apparatus 1 of the present embodiment.

The central processing unit (CPU) 43 shown in FIG. 2 executes a program, and thus, the X-ray CT apparatus 1 functions as an operation reception unit 51, a main scan condition setting unit 52, a table-top movement control unit 53, and a main scan execution unit 54, as shown in FIG. 5. All or part of the components 51 to 54 of the X-ray CT apparatus 1 may be provided in the X-ray CT apparatus 1 as hardware.

The operation reception unit 51 has a function of receiving from the input device 42 an instruction for three-dimensionally sliding the projector unit 33. The operation reception unit 51 has a function of receiving from the input device 42 an instruction for changing a cone angle of laser light. The operation reception unit 51 has a function of receiving from the input device 42 an instruction for changing a fan angle of laser light. The operation reception unit 51 has a function of receiving from the input device 42 an instruction for changing a tilt angle of the projector unit 33.

The main scan condition setting unit 52 has a function of setting main scan conditions to be used in a main scan, based on the instructions received by the operation reception unit 51. Examples of the main scan conditions include X-ray tube voltage, X-ray tube current, slice thickness, a cone angle, a fan angle, a gantry tilt angle, a reconstruction matrix, a main scan position, and a main scan range from a scan start position to a scan end position.

The main scan condition setting unit 52 sets a position of the projector unit 33 by sliding the projector unit 33 via the projector controller 36, based on an instruction received by the operation reception unit 51. In other words, the main scan condition setting unit 52 three-dimensionally slides the projectors 33A to 33C as one body. Here, the main scan condition setting unit 52 may set positions of two projector units 33.

Figure 6:
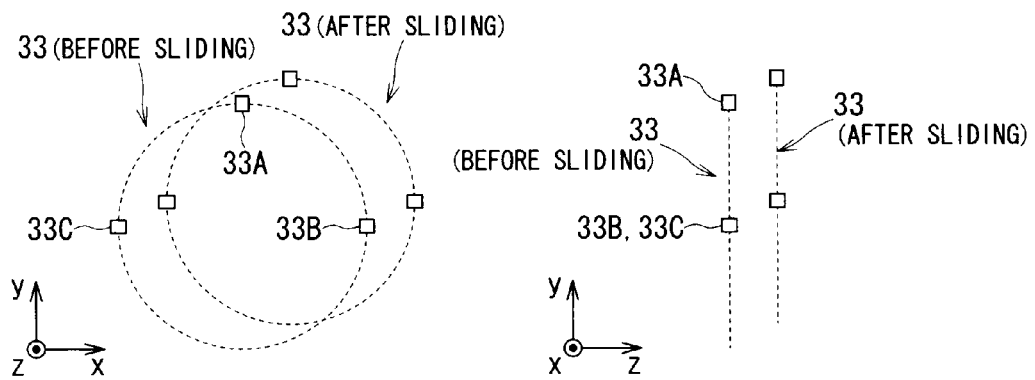
FIG. 6 is a diagram for explaining sliding of the projector unit in the X-ray CT apparatus of the present embodiment.

FIG. 6 is a diagram for explaining sliding of the projector unit 33 in the X-ray CT apparatus 1 of the present embodiment.

An x-y plane view showing the sliding of the projector unit 33 is shown on a left side in FIG. 6. A y-z plane view showing the sliding of the projector unit 33 is shown on a right side in FIG. 6.

As shown in FIG. 6, the projector unit 33 can be three-dimensionally slid by a drive mechanism (not shown). In other words, the projectors 33A to 33C can be three-dimensionally slid as one body.

In addition, the main scan condition setting unit 52 shown in FIG. 5 sets a cone angle of laser light by changing the cone angle of the laser light via the projector controller 36, based on the instruction received by the operation reception unit 51. The main scan condition setting unit 52 sets a fan angle of laser light by changing the fan angle of the laser light via the projector controller 36, based on the instruction received by the operation reception unit 51. The main scan condition setting unit 52 sets a tilt angle of the projector unit 33 by changing the tilt angle of the projector unit 33 via the projector controller 36, based on the instruction received by the operation reception unit 51.

Figure 7:
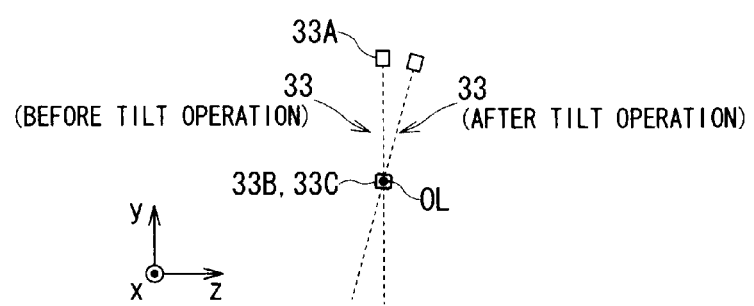
FIG. 7 is a diagram for explaining a tilt operation of the projector unit in the X-ray CT apparatus of the present embodiment.

FIG. 7 is a diagram for explaining a tilt operation of the projector unit 33 in the X-ray CT apparatus 1 of the present embodiment.

As shown in FIG. 7, the projector unit 33 can be tilted by a drive mechanism (not shown), with a direction of an x-axis passing through the projection center OL being an axis center. In other words, the projectors 33A to 33C can be tilted as one body, with the direction of the x-axis passing through the projection center OL being the axis center.

Figure 8:
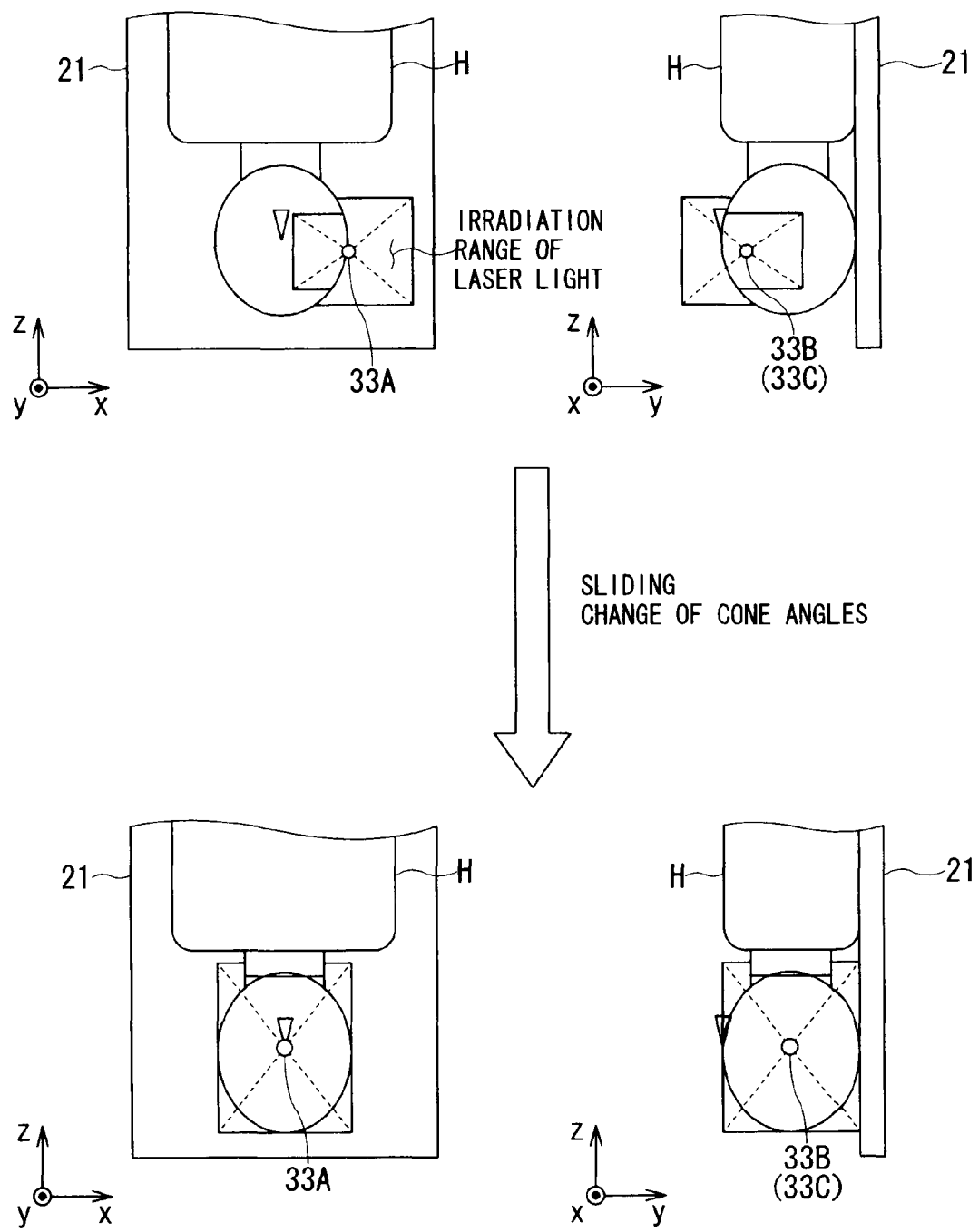
FIG. 8 is a diagram for explaining a method for setting a main scan range of an object by the X-ray CT apparatus of the present embodiment.

FIG. 8 is a diagram for explaining a method for setting a main scan range of the object H by the X-ray CT apparatus 1 of the present embodiment.

As shown in FIG. 8, the health professional slides the projector unit 33 in the x-axis direction, the y-axis direction, and the z-axis direction, via the input device 42, so that a head, a main scan site of the object H, is irradiated by laser light, while seeing the laser light from the projectors 33A to 33C of the projector unit 33. Alternatively, the health professional moves the object H on the table-top 21 in the x-axis direction and the z-axis direction so that the head, the main scan site of the object H, is irradiated by the laser light, while seeing the laser light from the projectors 33A to 33C of the projector unit 33. Then, the main scan condition setting unit 52 sets the position of the projector unit 33.

In addition, the health professional changes the cone angles and fan angles of the projectors 33A to 33C via the input device 42 so that the entire head, the main scan site of the object H, is irradiated by the laser light, while seeing the laser light from the projectors 33A to 33C of the projector unit 33. Then, the main scan condition setting unit 52 sets the cone angles and fan angles of the projector unit 33.

In the example shown in FIG. 8, the projector unit 33 is moved in the x-axis direction, the y-axis direction, and the z-axis direction, and the cone angles of the projector unit 33 are widened so that the laser light covers the entire head.

As described referring to FIG. 8, the health professional aligns the main scan site of the object H, based on irradiation of laser light from the projector unit 33 to the main scan site of the object H.

The table-top movement control unit 53 shown in FIG. 5 has a function of three-dimensionally sliding the table-top 21, via the table-top controller 22, by a difference between a position of the projection center OL of the projector unit 33 whose position is set by the main scan condition setting unit 52 and a position of the rotation center OX of the X-ray focal point of the X-ray source 31. At a point when the alignment of the main scan site of the object H based on irradiation of laser light is completed, as described referring to FIG. 8, the health professional performs a predetermined operation (for example, pushes down a predetermined switch), using the input device 42. Then, the table-top 21 is slid in the x-axis direction, the y-axis direction, and the z-axis direction, by the difference between the position of the projection center OL and the position of the rotation center OX of the X-ray focal point of the X-ray source 31.

When positions of two projector units 33 are set by the main scan condition setting unit 52, the table-top movement control unit 53 slides the table-top 21 by a difference between a projection center OL of the projector unit 33 at one of the set positions of the two and the rotation center OX of the X-ray focal point of the X-ray source 31.

The main scan execution unit 54 has a function of executing a main scan via the X-ray system controller 35, based on the main scan conditions set by the main scan condition setting unit 52.

When the positions of two projector units 33 are set by the main scan condition setting unit 52, the main scan execution unit 54 sets a position of the table-top 21 after being slid by the table-top movement control unit 53 as a start position of a scan. On the other hand, the main scan execution unit 54 sets the other of the set positions of the two as an end position of the scan. In other words, when the positions of two projector units 33 are set by the main scan condition setting unit 52, the main scan execution unit 54 scans a main scan range from the scan start position to the scan end position.

As described above, the X-ray CT apparatus 1 positions the object H by irradiating laser light simulating an irradiation range of an X-ray to the object H, using the projector unit 33, before a main scan. Therefore, with the X-ray CT apparatus 1, an optimum position, a cone angle, a fan angle, and a tilt angle for a main scan can be set without a scanogram scan before the main scan. Thus, unnecessary exposure of the object H to radiation provided by a scanogram scan can be eliminated.

With a conventional X-ray CT apparatus, first, a health professional sets any number of scanogram scan ranges, and sequentially stores them in the apparatus. Next, the health professional obtains scanograms according to the stored scanogram scan ranges. When a plurality of scanogram scan ranges are set, scanograms corresponding to them are continuously obtained. Thus, the health professional obtains scanograms of only a vicinal region where he intends to obtain tomographic images of the object H. The health professional sets main scan conditions, referring to the obtained scanograms, and performs a main scan, based on the set main scan conditions. A diagnosis is made using tomographic images obtained in this manner. At this time, there is a disadvantage that an amount of exposure of a patient to radiation at a stage of a scan plan increases.

Figure 9:
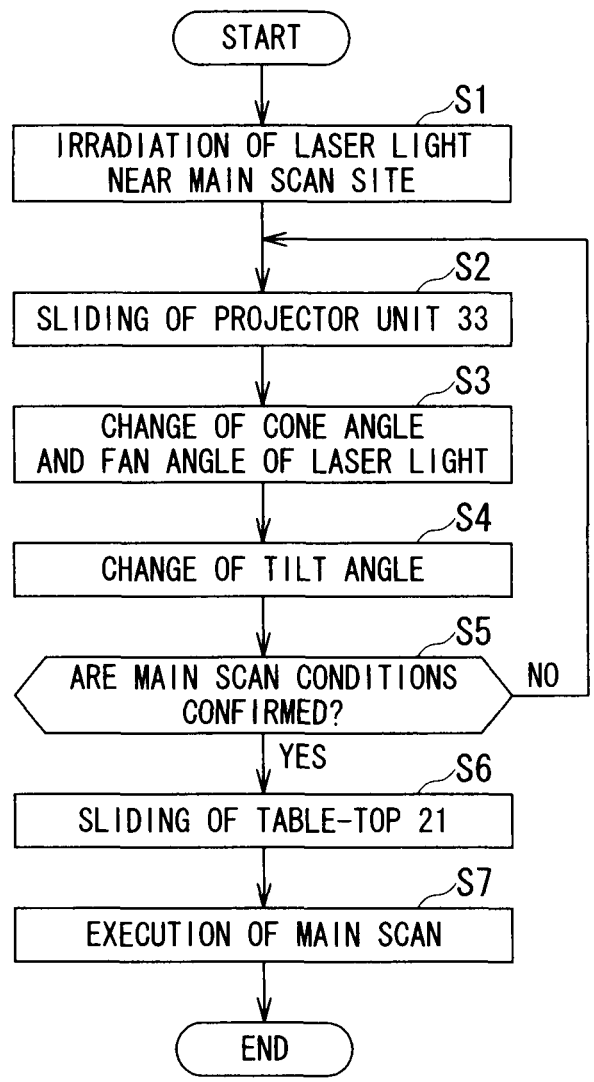
FIG. 9 is a flow chart showing operations of the X-ray CT apparatus of the present embodiment.

Next, operations of the X-ray CT apparatus 1 of the present embodiment will be described, based on a flow chart shown in FIG. 9.

First, the health professional places the object H to be subjected to a main scan on the table-top 21. The X-ray CT apparatus 1 moves the table-top 21 on which the object H is placed, based on an input signal input by the health professional via the input device 42, so that a main scan site of the object H is near a region of irradiation of laser light by the projector unit 33.

The X-ray CT apparatus 1 irradiates laser light from the projectors 33A to 33C of the projector unit 33 near the main scan site of the object H (step S1). In addition, the X-ray CT apparatus 1 slides the projector unit 33 via the projector controller 36, based on an instruction from the health professional (step S2).

In addition, the X-ray CT apparatus 1 changes a cone angle and fan angle of laser light via the projector controller 36, based on instructions from the health professional (step S3). Further, the X-ray CT apparatus 1 changes a tilt angle of the projector unit 33 via the projector controller 36, based on an instruction from the health professional (step S4). Steps S2 to S4 may be performed in any order, or part or all of steps S2 to S4 may be simultaneously performed.

Then, the X-ray CT apparatus 1 determines whether main scan conditions are confirmed by steps S2 to S4 or not, based on an instruction from the health professional (step S5). If the X-ray CT apparatus 1 determines YES, that is, determines that the main scan conditions are confirmed, by the determination in step S5, the X-ray CT apparatus 1 three-dimensionally slides the table-top 21, via the table-top controller 22, by a difference between a position of the projection center OL of the projector unit 33 set by step S2 and a position of the rotation center OX of the X-ray focal point of the X-ray source 31 (step S6).

Then, the X-ray CT apparatus 1 executes a main scan via the X-ray system controller 35, based on the main scan conditions confirmed by step S5 based on steps S2 to S4 (step S7).

On the other hand, if the X-ray CT apparatus 1 determines NO, that is, determines that the main scan conditions are not confirmed, by the determination in step S5, the X-ray CT apparatus 1 changes the main scan conditions (steps S2, S3, and S4).

In this manner, in a case where the X-ray CT apparatus 1 performs a volume scan of a head or the like, when one scan can cover the entire head, a position of the object H can be efficiently set, without the object H feeling uncomfortable, by setting a main scan region, referring to a region of irradiation of laser light by the projectors 33A to 33C. In addition, the health professional can determine a cone angle, a fan angle, and a tilt angle at a time of a main scan, based on the region of irradiation of laser light by the projectors 33A to 33C, without executing a scanogram scan. Thus, an amount of exposure of the object H to radiation provided by a scanogram scan can be eliminated.

According to the X-ray CT apparatus 1 in this embodiment, by illuminating an X-ray irradiation range of a main scan by the projectors 33A to 33C in setting the object H, the health professional can efficiently set the object H, while accurately recognizing the X-ray irradiation range.

In addition, according to the X-ray CT apparatus 1 in this embodiment, it is not necessary to execute a scanogram scan, and therefore, an amount of exposure of the object H to radiation provided by a scanogram scan can be eliminated.

While certain embodiments have been described, these embodiments have been presented by way of example only, and are not intended to limit the scope of the inventions.

Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
an X-ray irradiator configured to irradiate an object with an X-ray;
an X-ray detector configured to detect the irradiated X-ray;
a table on which the object is placed;
a rotation control unit configured to rotate the X-ray irradiator and the X-ray detector as one body around the object;
a plurality of projectors each having a light source on a circumference having a same radius as a rotation radius of an X-ray focal point of the X-ray irradiator and each configured to irradiate an irradiation range simulating an irradiation range of the X-ray with laser light;
a reception unit configured to receive an instruction for three-dimensionally sliding the plurality of projectors as one body;
a setting unit configured to set a position of the plurality of projectors by sliding the plurality of projectors on a basis of the received instruction;
a supporter configured to support the table and three-dimensionally slide the table by a difference between a position of a center of the circumference of the set plurality of projectors and a position of a rotation center of the X-ray focal point of the X-ray irradiator; and
a scan execution unit configured to execute a scan with the table after the sliding as a scan position.

2. The X-ray CT apparatus according to claim 1, wherein
the reception unit receives an instruction for changing a cone angle of the laser light,
the setting unit sets the cone angle of the laser light by changing the cone angle of the laser light, and
the scan execution unit executes the scan by setting the set cone angle as a cone angle of the X-ray.

3. The X-ray CT apparatus according to claim 1, wherein
the reception unit receives an instruction for changing a tilt angle of the plurality of projectors,
the setting unit sets the tilt angle of the plurality of projectors by changing the tilt angle of the plurality of projectors, and
the scan execution unit executes the scan according to the set tilt angle.

4. The X-ray CT apparatus according to claim 1, wherein
the reception unit receives an instruction for changing a fan angle of the laser light,
the setting unit sets the fan angle of the laser light by changing the fan angle of the laser light, and
the scan execution unit executes the scan by setting the set fan angle as a fan angle of the X-ray.

5. The X-ray CT apparatus according to claim 1, wherein
the plurality of projectors are provided in the supporter side from the X-ray irradiator.

6. The X-ray CT apparatus according to claim 1, wherein
the setting unit sets positions of two sets of the plurality of projectors,
the supporter slides the table by a difference between a center of the circumference of the projectors at one of the set positions of the two sets and the rotation center of the X-ray focal point of the X-ray irradiator, and
the scan execution unit sets the table after the sliding as a start position of the scan and sets the other of the set positions of the two sets as an end position of the scan.

7. The X-ray CT apparatus according to claim 1, wherein
the plurality of projectors are three projectors having the light source at an upper end position in a vertical direction on the circumference and positions at a same height as the circumference center, respectively.

8. A control method of an X-ray CT apparatus comprising:
a first step of receiving an instruction for three-dimensionally sliding a plurality of projectors as one body, which each has a light source on a circumference having a same radius as a rotation radius of an X-ray focal point of an X-ray irradiator which irradiates an object with an X-ray and each irradiates an irradiation range simulating an irradiation range of the X-ray with laser light;
a second step of setting a position of the plurality of projectors by sliding the plurality of projectors on a basis of the received instruction;
a third step of three-dimensionally slide a table on which the object is placed, by a difference between a position of a center of the circumference of the set plurality of projectors and a position of a rotation center of the X-ray focal point of the X-ray irradiator; and
a fourth step of executing a scan with the table after the sliding as a scan position.

9. The control method of the X-ray CT apparatus according to claim 8, wherein
the first step receives an instruction for changing a cone angle of the laser light,
the second step sets the cone angle of the laser light by changing the cone angle of the laser light, and
the fourth step executes the scan by setting the set cone angle as a cone angle of the X-ray.

10. The control method of the X-ray CT apparatus according to claim 8, wherein
the first step receives an instruction for changing a tilt angle of the plurality of projectors,
the second step sets the tilt angle of the plurality of projectors by changing the tilt angle of the plurality of projectors, and
the fourth step executes the scan according to the set tilt angle.

11. The control method of the X-ray CT apparatus according to claim 8, wherein
the first step receives an instruction for changing a fan angle of the laser light,
the second step sets the fan angle of the laser light by changing the fan angle of the laser light, and
the fourth step executes the scan by setting the set fan angle as a fan angle of the X-ray.

12. The control method of the X-ray CT apparatus according to claim 8, wherein
the second step sets positions of two sets of the plurality of projectors,
the third step slides the table by a difference between a center of the circumference of the projectors at one of the set positions of the two sets and the rotation center of the X-ray focal point of the X-ray irradiator, and
the fourth step sets the table after the sliding as a start position of the scan and sets the other of the set positions of the two sets as an end position of the scan.

13. The control method of the X-ray CT apparatus according to claim 8, wherein
the first step irradiates the irradiation range with the laser light from three projectors having the light source at an upper end position in a vertical direction on the circumference and positions at a same height as the circumference center, respectively.

* * * * *